United States Patent [19]

Mehra

[11] Patent Number: 5,165,403
[45] Date of Patent: Nov. 24, 1992

[54] DIFIBRILLATION LEAD SYSTEM AND METHOD OF USE

[75] Inventor: Rahul Mehra, Stillwater, Minn.

[73] Assignee: Medtronic, Inc., Minneapolis, Minn.

[21] Appl. No.: 661,568

[22] Filed: Feb. 26, 1991

[51] Int. Cl.⁵ ............................................. A61N 1/39
[52] U.S. Cl. .................................. 128/419 D; 128/786
[58] Field of Search .................. 128/419 D, 784, 785, 128/786

[56] References Cited

U.S. PATENT DOCUMENTS

| | | | |
|---|---|---|---|
| 3,729,008 | 4/1973 | Berkovits | 128/419 P |
| 4,402,330 | 9/1983 | Lindemans | 128/786 |
| 4,817,634 | 4/1989 | Holleman et al. | 128/784 |
| 4,953,551 | 9/1990 | Mehra et al. | 128/419 D |

OTHER PUBLICATIONS

"A Muttiekctrode—Time Sequential Laboratory Defibrillator for the Study of Implanted Electrode Systems" by Schuder et al., Transactions of the American Society of Artificial Organs, 161 XVII pp. 514–519, 1972.

"High Energy Transcatheter Cardioversion of Chronic Atrial Fibrillation" by Levy et al, JACC vol. 12, No. 2 pp. 514–518.

Internal Defibrillation of the Atrium: Importance of Electrode Position, by P. Jacob Varghese Abstract.

*Primary Examiner*—Kylel Howell
*Assistant Examiner*—Scott M. Getzow
*Attorney, Agent, or Firm*—Reed A. Duthler; Harold R. Patton

[57] ABSTRACT

A method of cardioverting the atrium of a human heart, comprising insertion of first and second elongated electrodes tranvenously into the heart and associated vessels. One electrode is preferably located in the coronary sinus and great vein of the heart. The other electrode is preferably located in the vicinity of the atrium of the heart, spaced from the electrode located in the coronary sinus. In response to detection of fibrillation or in response to manual triggering, a defibrillation pulse is applied between the first and second electrodes to effect atrial cardioversion.

7 Claims, 4 Drawing Sheets

DIFIBRILLATION LEAD SYSTEM AND METHOD OF USE

BACKGROUND OF THE INVENTION

The present invention relates to medical electrical leads generally, and more particularly to implantable defibrillation electrodes and leads.

Early concepts of implantable defibrillators, such as disclosed in Reissue Pat. No. 27,652 by Mirowski, et al, envision an electrode system employing a ventricular endocardial electrode and a plate electrode mounted to the heart directly, subcutaneously, or to the skin. However, it has long been recognized that a totally transvenous system would be desirable in order to simply the use of implantable defibrillators. One such system is suggested in Mirowski, et al U.S. Pat. No. 3,942,536, which discloses a transvenous lead having electrodes intended for location in the right ventricular apex and in the superior vena cava. This electrode system is disclosed as useful for either ventricular or atrial defibrillation. Such systems were eventually tested in human beings, with some success. However, currently available implantable defibrillators typically employ epicardial patch electrodes, alone, or in conjunction with transvenous electrodes.

While systems employing epicardial patch electrodes are workable, a thoracotomy is required in order to apply the epicardial electrodes. It is generally believed that it would be desirable to produce an implantable defibrillation system which entirely avoids the necessity of a thoracotomy, and there has been substantial work directed towards development of such systems, as disclosed in Kallok U.S. Pat. No. 4,727,877, Tacker, et al U.S. Pat. No. 4,708,145, and as disclosed in U.S. application Ser. No. 07/284,957 filed Dec. 15, 1988 by Mehra, for an "Endocardial Defibrillation Electrode System". Other endocardial defibrillation electrodes are disclosed in Gold et al U.S. Pat. No. 4,481,953, Kinney, et al U.S. Pat. No. 4,161,952, Kiekhafer et al U.S. Pat. No. 4,934,049 and in U.S. Pat. application Ser. No. 07/479,928, filed Feb. 14, 1990 by Holleman, et al, for an "Implantable Electrode and Method for Fabrication". The Kinney, Gold and Kiekhafer patents and the Holleman, et al application all disclose endocardial defibrillation leads employing defibrillation electrodes fabricated from elongated coils of biocompatible metal, mounted exposed to the exterior of the defibrillation lead, for location in the right ventricle and other locations within the heart. The above-cited Smits patent and the Mehra application both disclose a variety of endocardial defibrillation electrodes intended for use in the atrium, ventricle and coronary sinus, all of which employ electrodes taking the form of elongated coils of conductive biocompatible metals.

Concurrent with the development of lead systems adapted to treat ventricular fibrillation, there has also been some work directed to the development of lead systems to treat atrial fibrillation. Synchronized cardioversion using two electrodes located on a lead located in the right atrium is disclosed in Charms U.S. Pat. No. 3,738,370. A later system is disclosed in Mirowski et al U.S. Pat. No. 3,952,750, employing one electrode in the atrium and presumably a second electrode at an unspecified location. Neither of these references discloses a specific embodiment for the electrodes located in the atrium.

An electrode lead system specifically designed for atrial defibrillation is disclosed in the article "Elective Countershock in Atrial Fibrillation With an Intracardiac Electrode—A Preliminary Report, by Jain, et al, published in the *Journal of the Association of Physicians of India*, Vol. 18, pp 821–824, 1970. This lead was provided with a 10 mm silver electrode for location in the right atrium and was tested in conjunction with either a second electrode located in the right atrium or a second, cutaneous electrode located on the left side of the chest wall. A second electrode system specifically designed for use in atrial cardioversion is disclosed in the article "Safety and feasibility of transvenous cardioversion in atrial tachycardia", by Blanc et al, published in *Cardiac Pacing*, edited by Gomez, Futura Pub. Co., 1985, pp 1526–1529. This electrode system employed a single lead with electrodes located in the atrium and pulmonary artery.

SUMMARY OF THE INVENTION

The present invention is directed toward the provision of an entirely endocardial defibrillation lead system particularly optimized for use in defibrillation or cardioversion of the atrium. However, the lead system may also be used in conjunction with other endocardial electrodes adapted to effect ventricular defibrillation. The system disclosed includes coronary sinus and right atrial electrodes, and may be embodied with the electrodes located on the same or different lead bodies.

Also disclosed are embodiments in which a ventricular electrode is provided so that defibrillation or cardioversion pulses may be delivered between the right ventricle and the coronary sinus electrode. In such embodiments, the atrial electrode may be located on the same lead as the coronary sinus or right ventricular electrode, or may be located on a separate lead.

DETAILED DESCRIPTION OF THE PREFERRED EMBODIMENTS

Figure 1:
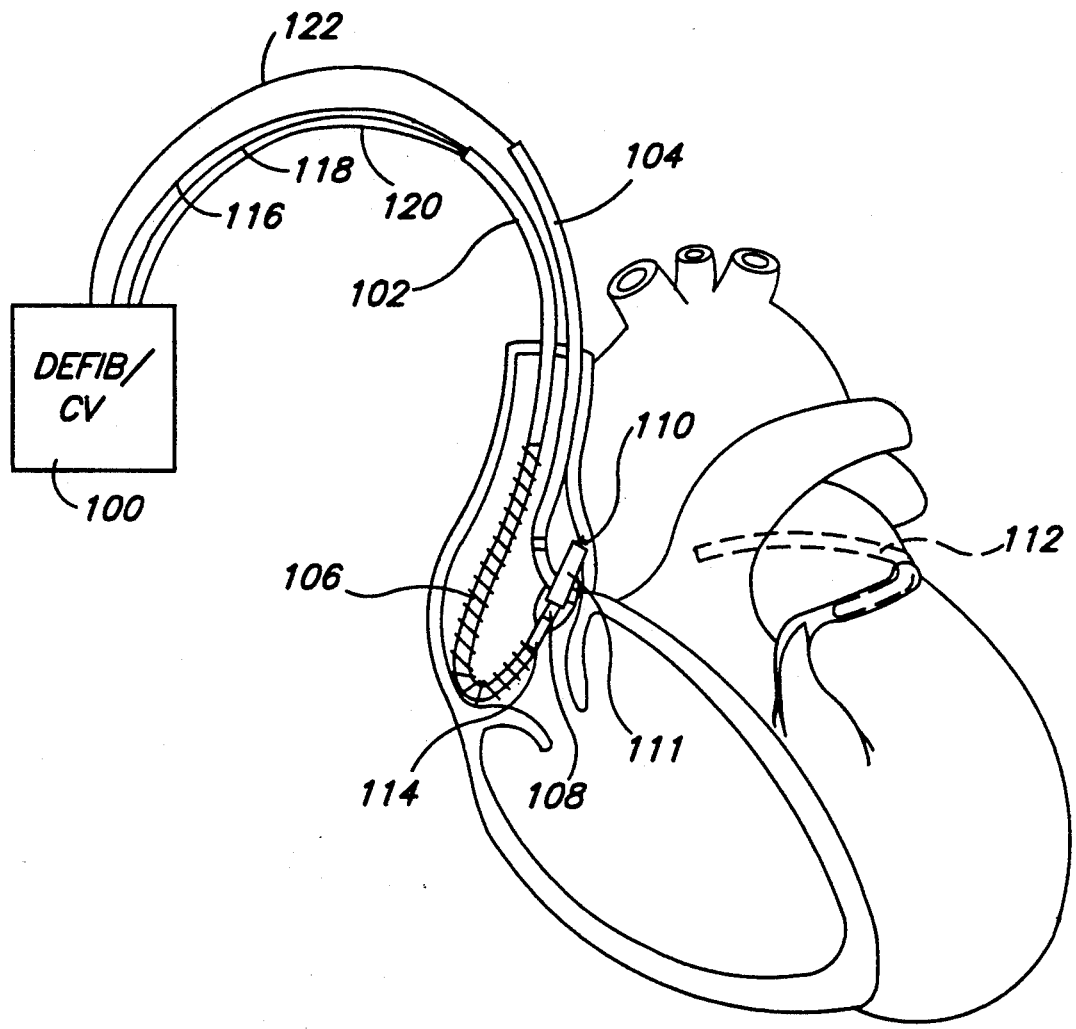
FIG. 1 illustrates a first embodiment of a cardioversion/defibrillation lead system according to the present invention employing a J-shaped atrial electrode located on a lead also provided with a pair of electrodes including a helical electrode for affixing the lead to the atrial wall and a separate lead carrying the coronary sinus electrode.

FIG. 1 is a cutaway view of the human heart in which a lead system embodying the present invention has been implanted. The lead system includes two leads, one having its electrode located in the right atrium, the other having its electrode located in the coronary sinus. The right atrial lead 101 employs an elongated insulative lead body 102, to which a coiled defibrillation electrode 106 has been mounted. The distal end of the lead includes an electrode head 111, carrying a helical electrode 110 and a ring electrode 108. The electrodes 106, 108 and 110 are coupled to an implantable defibrillator/cardioverter 100 by means of conductors 116, 118 and 120. The coronary sinus lead 103 also has an elongated insulative lead body 104 which carries a coiled defibrillation electrode at its distal end, located as generally indicated in broken outline at 112. Electrode 112 is located within the coronary sinus and the great cardiac vein. Preferably the proximal end of the electrode 112 is spaced about 3 to 8 cm from the opening of the coronary sinus into the right atrium. The curved configuration of lead 101 assists in providing an adequate surface area electrode within the atrium and the fixation helix assists in keeping the electrode 106 spaced from the opening of the coronary sinus. Depending on the size and configuration of the patient's heart, it is anticipated that the electrode 106 may extend into the superior vena cava or may be located predominantly in the superior vena cava. Maintaining an appropriate spacing between the electrodes 112 and 106 is important to avoid areas of excessive current density in the regions of their closest proximity.

The electrode 112 is coupled to an implantable defibrillator cardioverter 100 by means of conductor 122. Electrodes 108 and 110 are used by defibrillator cardiovertor 100 to sense the electrical activity of the atrium and to diagnose the presence of atrial tachycardias or atrial fibrillations requiring cardioversion or defibrillation, respectively. In response to the detection of tachycardia or fibrillation, defibrillator/cardioverter 100 generates a high voltage pulse between electrodes 106 and 112.

Lead body 102 contains 3 concentric coiled conductors 116, 118, 120, illustrated schematically. These three conductors are separated from one another by tubular insulative sheaths. This tripolar arrangement is illustrated in more detail in Kallok, et al U.S. Pat. No. 4,355,646, incorporated herein by reference in its entirety. As set forth in the cited Kallok, et al patent, the insulative sheaths employed in the present lead may be made of an implantable polyurethane. However, in some embodiments, the sheaths may be made of silicone rubber or other implantable, flexible plastic. The conductor coils may be made of Drawn Brazed Strand wire (DBS), previously used in cardiac pacing leads or may be another implantable metal such as MP35N alloy, also commonly used in pacing leads.

The outermost of the three conductor coils within lead body 102 is coupled to the proximal end of electrode coil 106 and the middle coil within sheath 102 is coupled to ring electrode 108. The innermost coil within lead body 102 is mounted rotatably within an insulative sheath separating the innermost coil from the middle coil, and is mechanically and electrically coupled to helical electrode 110, which is retractably mounted within electrode head 111. Rotation of the innermost conductor coil causes rotation of electrode 110 and advancement of electrode 110 out the distal end of electrode head 111. Electrode 110 may be screwed into the tissue of the right atrial appendage of the heart, and is used to anchor the lead. The electrode head 111, electrode 110, and the inner most conductor coil employed to rotate the helical electrode 110 are described in more detail in Bisping U.S. Pat. No. 4,106,512, issued Aug. 15, 1978, incorporated herein by reference in its entirety.

Lead body 104 contains a single coiled conductor, coupled to the proximal end of an electrode coil illustrated in broken outline at 112. This conductor coil may optionally extend within sheath to the proximal end of the lead, and may also be coupled to the distal end of the electrode 112. At the distal end of the lead is an insulative plastic tip, not visible in this view.

Electrodes 106 and 112 may be mounted around insulative lead bodies 102 and 104 and bonded to them by means of a backfill of insulative plastic, as described in Kiekhafer, et al U.S. Pat. No. 4,934,049, on Jun. 19, 1990, and incorporated herein by reference in its entirety. As an alternative, the insulative lead bodies 102 and 104 may be fabricated of a polyurethane or other heat flowable material, expanded against the interior of the electrode coils under pressure and heat to allow the material of the sheath to flow between the electrode coils, as illustrated in U.S. Pat. application Ser. No. 07/479,928, filed on Feb. 14, 1990 for an "Implantable Electrode and Method for Fabrication" by Holleman, et al, also incorporated herein by reference in its entirety. Alternatively, the electrode coils may be fabricated using the techniques illustrated in the above cited Kinney or Gold patents. Electrodes 30 and 32 are preferably made of platinum. However, as discussed in the references cited above, other implantable metals have been disclosed for use in such electrodes.

The curved configuration of electrode 106 as illustrated is maintained by any of a number of known mechanisms. It may be maintained by means of molding lead body 102 in the form of a curved tube, or otherwise imparting a predetermined curve thereto. For example, the techniques illustrated in Berkovitz U.S. Pat. No. 3,729,008, also incorporated herein by reference in its entirety may ba adapted. Alternatively, the electrode coil 106 may be preformed to exhibit a curved configuration. An additional preformed curved coil devoted particularly to maintaining the curved configuration of the lead may also be used, as disclosed in Lindemans U.S. Pat. No. 4,402,330, issued on Sep. 6, 1983, also incorporated herein by reference in its entirety.

A specific example of a defibrillation pulse generator which may be used in conjunction with the present lead is disclosed in Mehra et al U.S. Pat. No. 4,953,551, issued on Sep. 4, 1990, incorporated herein by reference in its entirety. An addition example of an appropriate pulse generator is disclosed in U.S. Pat. application Ser. No. 07/612,758 for an "Apparatus for Delivering Single & Multiple Cardioversion Pulses", filed Nov. 14, 1990, by Keimel and also incorporated herein by reference in its entirety.

While it is envisioned that the present application may most beneficially be practiced in conjunction with an implantable cardioverter/defibrillator which has the capability of sensing the electrical activity of the heart to detect the presence of atrial tachycardia or fibrillation, the invention may also be usefully practiced in conjunction with a device as disclosed in Mirowski et al U.S. Pat. No. 3,952,750, issued on Apr. 27, 1976, incorporated herein by reference in its entirety. In devices as illustrated in the Mirowski et al. patent, the detection of atrial fibrillation is not accomplished by the implanted device. Instead, the presence of atrial fibrillation is detected either by a physician or the patient, and a signal is generated external to the device, triggering delivery of a synchronized atrial defibrillation pulse. This approach is made possible by the fact that atrial fibrillation, unlike ventricular fibrillation, does not result in the cessation of the heart's pumping action.

Figure 2:
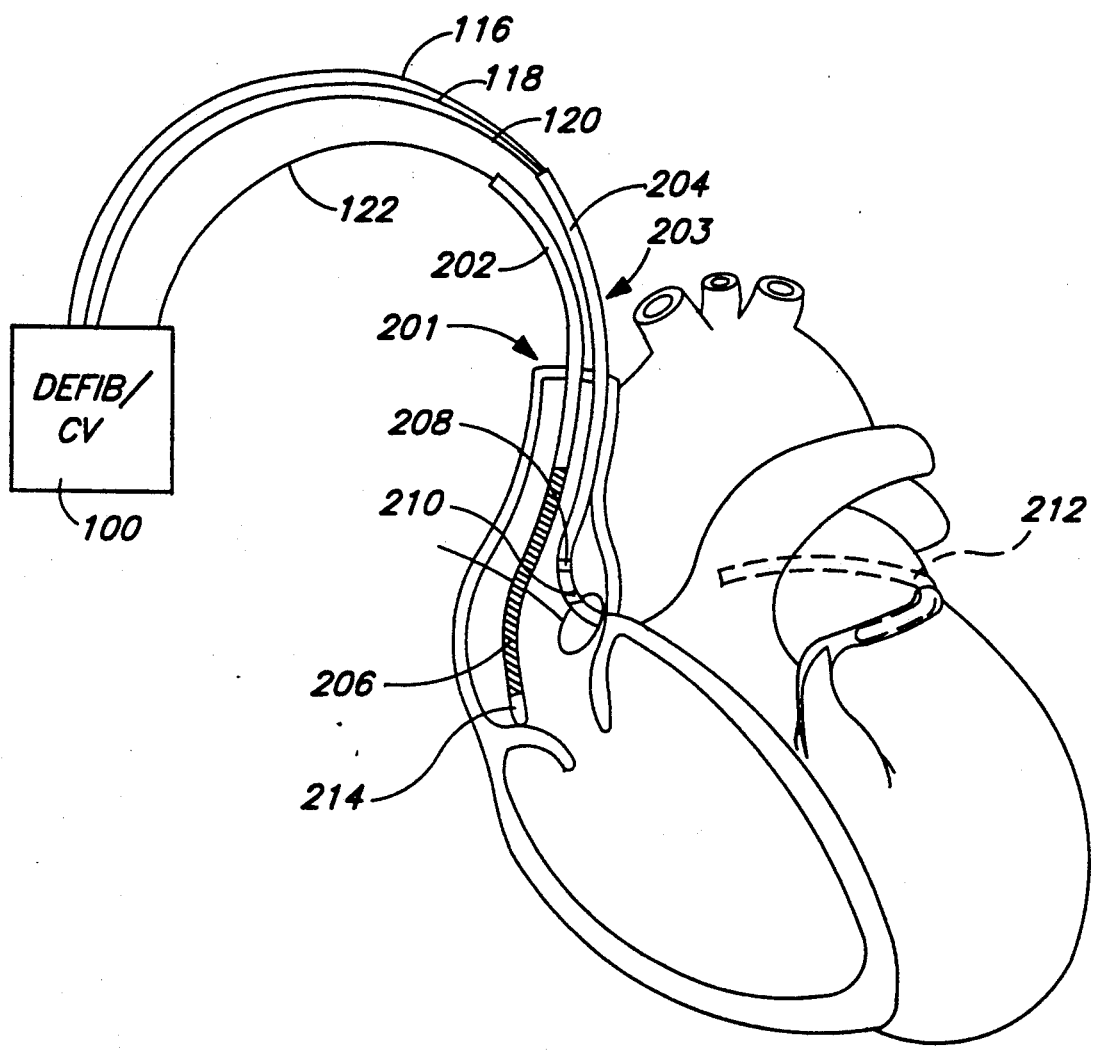
FIG. 2 illustrates a second embodiment of a cardioversion/defibrillation lead system according to the present invention, employing a generally straight atrial electrode, not actively affixed to the atrial wall.

FIG. 2 is a cutaway view of the human heart illustrating an alternative embodiment of the present invention employing an atrial lead having a generally straight defibrillation electrode 206 and a coronary sinus defibrillation lead 203 provided with sensing electrodes 208 and 210. The electrode lead 203 may correspond to the coronary sinus defibrillation lead illustrated in FIG. 2 of allowed U.S. Pat. application Ser. No. 07/284,957, filed Dec. 15, 1988 by Mehra, for an "Endocardial Defibrillation Electrode System" incorporated herein by reference. Like the atrial lead 101 discussed in conjunction with FIG. 1, lead 203 has a tripolar configuration, employing three coaxial conductors 116, 118 and 120, each coupled to one of electrodes 208, 210 and electrode 212, indicated in broken out line within the coronary sinus. Electrodes 208 and 210 function to sense the electrical activity of the atrium of defibrillation detection and/or cardiac pacing.

Electrode lead 201 corresponds to the lead illustrated in FIG. 2 of the above-cited allowed application by Mehra et al., however it omits sensing electrodes corresponding to electrodes 208 and 210, and includes only a single conductor 122, mounted within insulative lead body 202, coupled to electrodes 206. A pliant insulative tip 124 is visible. A corresponding pliant, insulative tip is located on the distal end of lead 203, not visible in this view and on the distal end of lead 101, FIG. 1. As in the case of electrode 106, FIG. 1, electrode 206 may extend proximally into the superior vena cava or may be located predominantly in the superior vena cava.

The construction of electrodes 206 and 212 corresponds to the construction of electrodes 106 and 112, as discussed above in conjunction with FIG. 1. As in the case of the system illustrated in FIG. 1, defibrillator/cardioverter 200 delivers defibrillation pulses between electrodes 206 and 212, either in response to detection of atrial tachycardia or fibrillation via electrodes 208 and 210 or in response to an external command signal.

Figure 3:
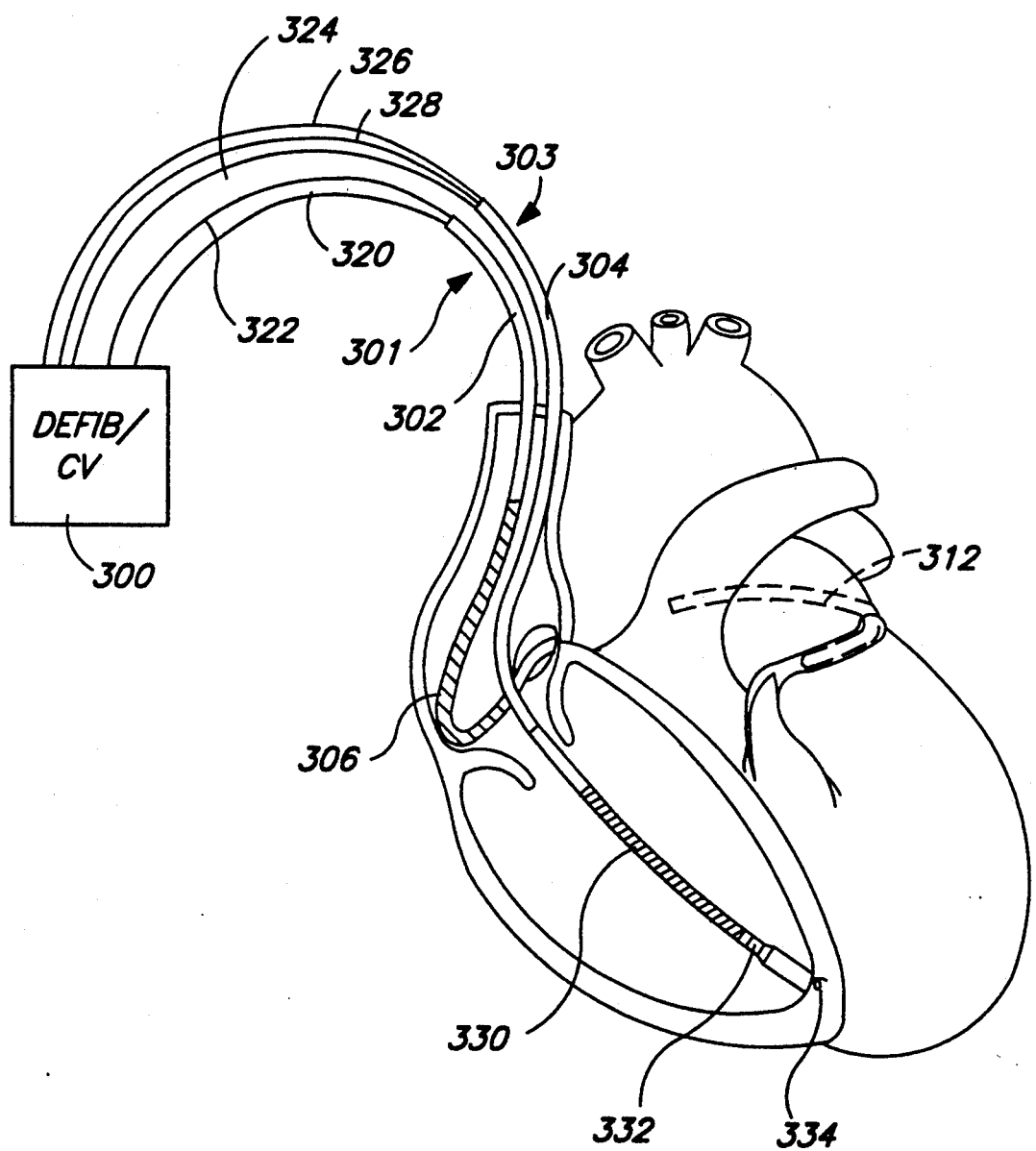
FIG. 3 illustrates a third embodiment of a cardioversion/defibrillation lead system according to the present invention, employing a lead carrying both the coronary sinus electrode and the atrial electrode in conjunction with a ventricular defibrillation lead.

FIG. 3 is a cutaway view of the heart illustrating yet another embodiment of an electrode system embodying the present invention. In this embodiment, a first electrode lead 301 is provided with two defibrillation electrodes 306 and 312, both located around its insulative lead body 302. Lead 301 is a bipolar lead, employing two conductors 320 and 322 located coaxially within lead body 302. Electrodes 306 and 312 may correspond to electrodes 106 and 112, illustrated in FIG. 1. Electrode 306 is provided with a preformed, J-shaped configuration corresponding to that of electrode 106, illustrated in FIG. 1 which assists both in maintaining the lead in its location within the heart and allows for a substantial surface area of the electrode 306 to be located in the right atrium, while remaining spaced from the ostium of the coronary sinus. Electrode 312 is located within the coronary sinus and great vein also, spaced from the ostium of the coronary sinus. An interelectrode spacing of at least about 5 cm is believed desirable. This assists in providing good intraelectrode separation between electrode 306 and 312. As a practical matter, this interelectrode spacing may result in electrode 306 being predominantly located in the superior vena cava in some patients.

A second lead 303 is provided which is also triaxial lead in which three conductors, 324, 326 and 328 are located coaxially within insulative lead body 304. Each of these conductors is coupled to one of defibrillation electrode 330, ring electrode 332 or helical electrode 334. With the exception of the omission of the J-shaped bend, lead 303 corresponds exactly to lead 101, illustrated in FIG. 1.

As illustrated, this electrode system is provided with electrodes 332 and 334 allowing for sensing of ventricular electrical activity, but is not provided with a separate set of electrodes for sensing electrical activity in the atrium. As such, as illustrated, it is anticipated that the cardioverter/defibrillator 300 will automatically delivery high voltage pulses between electrode 330 and electrode 312 in response to detection of ventricular tachycardia or fibrillation. However, delivery of atrial cardioversion or defibrillation pulses between electrode 306 and electrode 312 would be triggered externally by the patient or a physician in response to detection of symptoms indicative of atrial fibrillation or atrial tachycardia. In such an embodiment, an internal override disabling the ability to trigger atrial cardioversion/defibrillation shocks may be desirable in response to internal detection of electrical activity which is reliably identified as ventricular tachycardia or ventricular fibrillation rather than rapid ventricular rates due to atrial fibrillation or atrial tachycardia.

Figure 4:
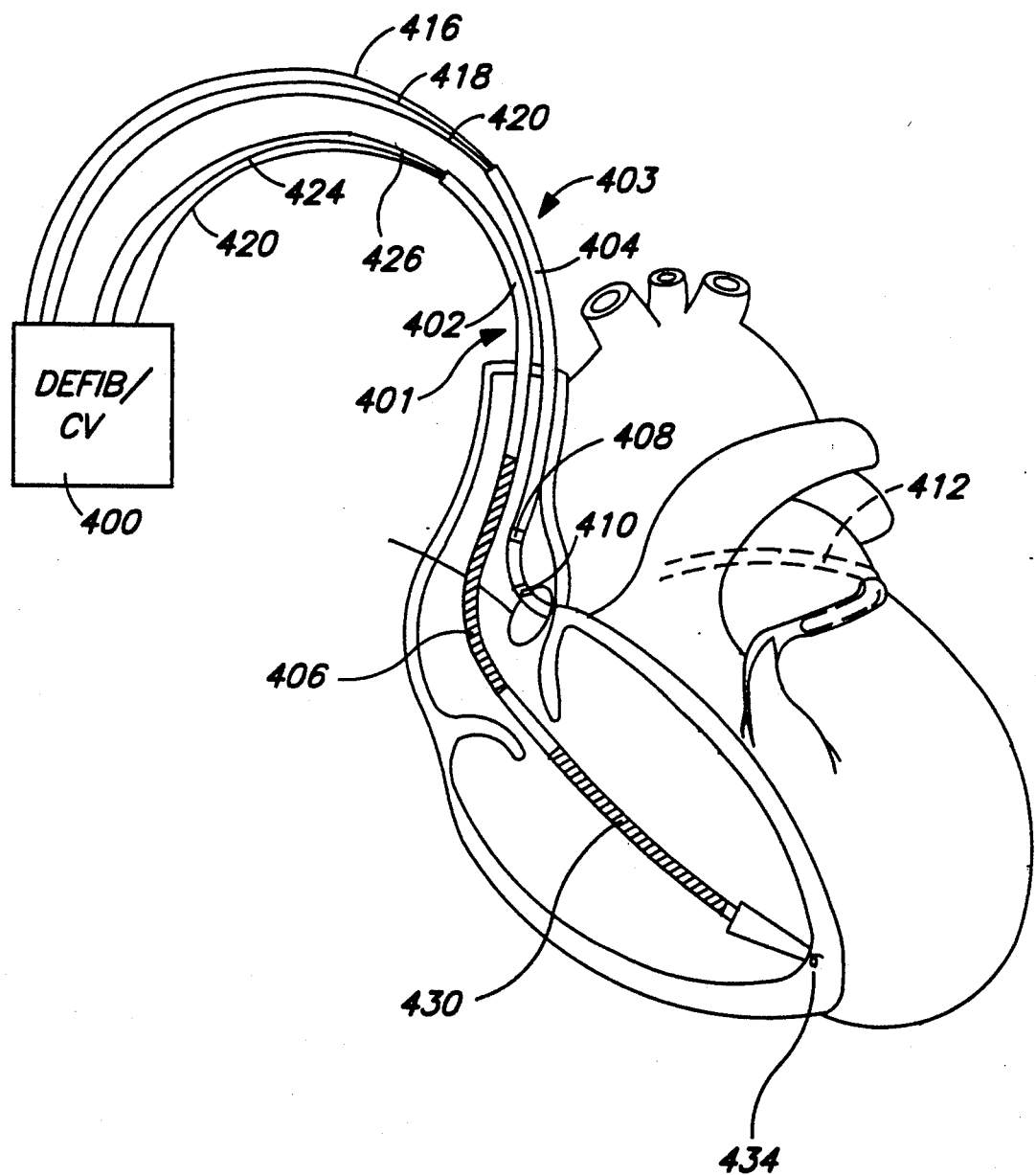
FIG. 4 illustrates a fourth embodiment of a cardioversion/defibrillation lead system according to the present invention, employing a lead carrying both a ventricular electrode and the atrial electrode in conjunction with a separate lead carrying the coronary sinus electrode.

FIG. 4 is a cutaway view of the heart illustrating yet another embodiment of the present invention. This embodiment includes a lead 401, which has defibrillation electrodes 406 and 430 mounted to its insulative lead body 402, and located in the right atrium and right ventricular, respectively. The lead also includes a helical electrode 434, corresponding to the helical electrode 110, illustrated in conjunction with lead 101, FIG. 1. As in the case of lead 101, illustrated in FIG. 1, lead 401 is a coaxial, tripolar lead having coaxial conductors 420, 424 and 426 coupled to electrodes 406, 430 and 434. Lead 403 corresponds exactly to lead 203, illustrated in FIG. 2 and is provided with ring electrodes 408 and 410 and with a defibrillation electrode, each coupled to one of three conductors 416, 418 and 420. It is anticipated that in some cases, this electrode configuration will be practiced by employing a lead as disclosed in the above cited Mirowski patent, employing right ventricular and SVC electrodes in conjunction with a coronary sinus lead as disclosed in the above cited Mehra application.

In this embodiment, the defibrillator/cardioverter 400 is configured such that it may sense electrical activity in the atrium via electrodes 408 and 410 and may sense electrical activity in the ventricular via electrode 434 and a remote, different electrode, or between electrode 434 and electrode 430. In response to detection of ventricular tachycardia, cardioverter/defibrillator 400 generates a high voltage pulse between electrodes 430 and 412. In response to detection of atrial tachycardia or fibrillation, defibrillator/cardioverter 400 delivers a high voltage between electrodes 406 and 412. As such, the lead system illustrated is particularly beneficial if atrial and ventricular cardioversion and defibrillation functions are desired to be combined within the same device. Selection between electrodes 406 and 430 may be accomplished using a defibrillation/cardioversion pulse generator as disclosed in the above-cited Keimel et al. application, or using other defibrillation pulse generators capable of being programmed to deliver pulses between multiple pairs of electrodes, as disclosed in the article "A Multielectrode—Time Sequential Laboratory Defibrillator for the Study of Implanted Electrode Systems", by Schuder et al, published in *Transac-*

*tions of the American Society of Artificial Organs*, Vol. XVIII, pp 514–519, 1972, incorporated herein by reference in its entirety.

The inventive atrial cardioversion and defibrillation lead system is shown in conjunction with an endocardial ventricular electrode, if ventricular defibrillation capabilities are desired. However, the endocardial ventricular electrode may be replaced by or augmented with a subcutaneous patch electrode, which may correspond to any of the previously known subcutaneous patch electrodes. Alternatively, if the atrial defibrillation system is to be added to a previously existing ventricular defibrillation lead system, the endocardial ventricular electrode may be substituted with a left ventricular epicardial electrode.

Appropriate epicardial electrodes are illustrated in Holleman et al U.S. Pat. No. 4,817,634, issued Apr. 4, 1989, and incorporated herein by reference in its entirety. Appropriate subcutaneous electrodes may take the form of the electrodes illustrated in U.S. Pat. application Ser. No. 07/376,730 by Lindemans et al, filed Jul. 7, 1989 for a "patch electrode", also incorporated herein by reference in its entirety. The location of the subcutaneous electrode will vary from patient to patient, depending upon the particular geometry of the patient's heart, the other electrodes present and other considerations of bodily structure.

As discussed above, the electrode system and its method of application may be beneficially practiced in a wide variety of contexts, including automatic and non-automatic cardioverters and defibrillators, which may or may not include additional electrodes dedicated toward provision of ventricular defibrillation pulses. Similarly, the electrodes employed to perform atrial defibrillation may be located on leads having a wide variety of configurations. While some of the configurations illustrated are specifically claimed below, these particular configurations should not be considered limiting with regard to claims to the general method set forth above or claims directed generally to lead systems appropriate for carrying out the claimed method. As such, the above illustrated embodiments should be considered exemplary, rather than limiting with regard to the claims presented below.

In conjunction with the above disclosure, I claim:

1. A method of cardioverting or defibrillating a heart, comprising;
   transvenously inserting a first elongated electrode into the great vein and coronary sinus of said heart;
   transvenously inserting a second elongated electrode into the atrium or superior vena cava of said heart, spaced from said first electrode; and
   delivering a cardioversion or defibrillation pulse between said first and second electrodes.

2. A method according to claim 1 wherein said step of inserting said first electrode comprises inserting a first lead carrying said first electrode and wherein said step of inserting said second electrode comprises inserting a second lead carrying said second electrode.

3. A method according to claim 1 or claim 2 wherein said step of inserting said first electrode comprises inserting said first electrode entirely within the coronary sinus and great vein of said heart and spaced from the opening of the coronary sinus into the atrium of said heart.

4. A method of cardioverting or defibrillating a heart, comprising;
   transvenously inserting a first elongated electrode into the great vein and coronary sinus of said heart;
   transvenously inserting a second elongated electrode into the atrium or superior vena cava of said heart, spaced from said first electrode; and
   delivering a cardioversion or defibrillation pulse between said first and second electrodes wherein said steps of inserting said first electrode and inserting said second electrode comprise inserting a single lead carrying said first and second electrodes such that said lead passes through the atrium of said heart and terminates in the great vein of said heart.

5. A method according to claim 1 or claim 2 or claim 4 wherein said step of inserting said second electrode comprises the step of inserting said second electrode into the atrium of said heart spaced from the opening of the coronary sinus into the atrium of said heart.

6. A method according to claim 1 or claim 2 or claim 4 further comprising locating a third electrode in or on the ventricles of said heart and wherein said step of delivering said cardioversion or defibrillation pulse comprises delivering said pulse only between said first and second electrodes.

7. A method according to claim 1 or claim 2 or claim 4 wherein said steps of inserting said first electrode and inserting said second electrode comprise inserting said first and second electrodes such that said first and second electrodes are s paced form one another and are located on opposite sides of the opening of the coronary sinus into the atrium of said heart.

* * * * *